United States Patent [19]

Phillips et al.

[11] Patent Number: 5,315,019

[45] Date of Patent: May 24, 1994

[54] CONTINUOUS PROCESS FOR THE MANUFACTURE OF 2,5-DIHYDROFURANS FROM γ, δ-EPOXYBUTENES

[75] Inventors: Gerald W. Phillips, Longview, Tex.; Stephen N. Falling, Kingsport, Tenn.; Stephen A. Godleski; John R. Monnier, both of Fairport, N.Y.

[73] Assignee: Eastman Chemical Company, Kingsport, Tenn.

[21] Appl. No.: 962,545

[22] Filed: Oct. 19, 1992

Related U.S. Application Data

[63] Continuation-in-part of Ser. No. 748,408, Nov. 19, 1991, abandoned.

[51] Int. Cl.$^5$ .......................................... C07D 307/28
[52] U.S. Cl. .................................................. 549/507
[58] Field of Search ........................................ 549/507

[56] References Cited

U.S. PATENT DOCUMENTS

| 3,932,468 | 1/1976 | Kurkov | 549/507 |
| 3,996,248 | 12/1976 | Wall et al. | 549/507 |
| 5,034,545 | 7/1991 | Fischer | 549/507 |
| 5,082,956 | 1/1992 | Monnier et al. | 549/507 |

*Primary Examiner*—C. Warren Ivy
*Assistant Examiner*—A. A. Owens
*Attorney, Agent, or Firm*—J. Frederick Thomsen; William P. Heath, Jr.

[57] ABSTRACT

Disclosed is a continuous process for the manufacture of 2,5-dihydrofurans by the isomerization of γ,δ-epoxyalkenes in the liquid phase in the presence of a catalyst system comprising an onium iodide compound and a Lewis acid and a process solvent comprising a mixture of the 2,5-dihydrofuran product of the process and an oligomer of the γ,δ-epoxyalkenes reactant.

17 Claims, No Drawings

CONTINUOUS PROCESS FOR THE MANUFACTURE OF 2,5-DIHYDROFURANS FROM γ, δ-EPOXYBUTENES

This application is a continuation-in-part of co-pending application Ser. No. 07/748,408 filed Nov. 19, 1991 now abandoned.

This invention pertains to a continuous process for the manufacture of 2,5-dihydrofurans by the isomerization of γ,δ-epoxyalkenes in the liquid phase. More specifically, this invention pertains to the continuous isomerization of γ,δ-epoxyalkenes in the presence of a catalyst system comprising an onium iodide compound and a Lewis acid and a process solvent comprising the 2,5-dihydrofuran product of the process and an oligomer of the γ,δ-epoxyalkene reactant.

The preparation of 3,4-epoxy-1-butene by the selective monoepoxidation of butadiene is described in U.S. Pat. Nos. 4,897,498 and 4,950,773. 2,5-Dihydrofuran may be hydrogenated as described in U.S. Pat. No. 4,962,210 to tetrahydrofuran, a valuable compound useful as a chemical process solvent and as an intermediate in the preparation of polymers such as poly(tetramethylene ether)glycol.

U.S. Pat. Nos. 3,932,468 and 3,996,248 disclose the production of 2,5-dihydrofurans by the rearrangement of γ,δ-epoxyalkenes, i.e., unsubstituted and substituted butadiene monoepoxide compounds, with a homogeneous catalyst system comprising hydrogen iodide or hydrogen bromide and a transition metal Lewis acid in an organic solvent. This process suffers from a number of disadvantages such as the use of corrosive hydrogen halides and the need for expensive, high-boiling tertiary amide solvents, e.g., N-methyl-2-pyrrolidinone, to dissolve the transition metal Lewis acid. We have found that the processes of U.S. Pat. Nos. 3,932,468 and 3,996,248 also converts a significant amount of 3,4-epoxy-1-butene to crotonaldehyde.

U.S. Pat. No. 5,082,956 discloses processes for the preparation of 2,5-dihydrofurans by isomerizing γ,δ-epoxyalkenes in the presence of catalyst systems comprising certain onium iodide compounds and, optionally, an inorganic Lewis acid and/or certain organometallic halide compounds. The disclosed processes include vapor phase processes wherein a vapor of the epoxyalkene reactant is passed through a reaction zone containing the catalyst system which is in the form of a molten salt or a film deposited on a non-acidic support material. This gas phase process employs an inert gas diluent such as nitrogen or helium and is conducted at a temperature above the melting point of the catalyst components, typically at a temperature of 130° to 150° C.

In another embodiment of the isomerization process disclosed in U.S. Pat. No. 5,082,956, γ,δ-epoxyalkenes are isomerized to dihydrofurans in the liquid phase using a solution of the above-described catalyst system in an extraneous, inert solvent and a temperature of 100° to 150° C. This procedure uses a hydrocarbon or halogenated hydrocarbon solvent, such as mesitylene, pseudocumene or dichlorobenzene, having a boiling point higher than the 2,5-dihydrofuran product to facilitate isolation of the product from the catalyst solution by distillation.

The use of the catalyst as a molten salt or as a film supported on an inert support requires relatively high process temperatures (above the melting point of the catalyst) at which formation of side-products and degradation of the catalyst is enhanced. The choice of compounds to be used as catalyst is also restricted by the requirement that they have a sufficiently low melting point to make their use feasible. The use of the supported catalyst also suffers from the inability to purge non-volatile, oligomeric side-products from the reaction zone. The use of the catalyst as a molten salt increases the material handling difficulties when purging or replenishing portions of the catalyst mixture. The use of an inert, gaseous diluent in the gas phase processes requires the separation of the inert gas and dihydrofuran product in the gaseous product stream. The use of the catalyst as a solution in a solvent having a boiling point higher than the dihydrofuran product also has certain disadvantages such as the introduction to the production system of an additional component which must subsequently be removed by distillation.

We have discovered that 2,5-dihydrofurans may be conveniently and economically prepared by a continuous process wherein a γ,δ-epoxyalkene is isomerized in the liquid phase in the presence of the above-described catalyst systems using as the process solvent a mixture comprising the 2,5-dihydrofuran product and an oligomer of the γ,δ-epoxyalkene reactant. The present invention therefore provides a continuous process for the manufacture of a 2,5-dihydrofuran by the steps comprising:

(1) continuously feeding a γ,δ-epoxyalkene to a reaction zone containing a solution of:
(A) a catalytic amount of a catalyst system comprising (i) an onium iodide and (ii) a Lewis acid selected from inorganic Lewis acids, an organotin (IV) compound, an organostibonium compound or a mixture thereof; and
(B) a process solvent system comprising the 2,5-dihydrofuran product and an oligomer of the γ,δ-epoxyalkene reactant; and (2) continuously removing a vapor comprising the 2,5-dihydrofuran product from the reaction zone solution;

wherein the liquid phase of the reaction zone is maintained at a temperature of about 65° to 160° C. and the concentration of the catalyst system in the reaction zone liquid is maintained at about 10 to 95 weight percent, based on the total weight of the reaction zone liquid. The oligomer component of the solvent system is a side-product of the isomerization process wherein a γ,δ-epoxyalkene reactant is rearranged to a 2,5-dihydrofuran. The oligomer is a low molecular weight polyether which is normally not volatilized during the operation of the isomerization process or during the separation of the 2,5-dihydrofuran product from the crude reaction mixture by conventional vapor„liquid separation techniques. The polyether oligomer is the result of ring-opening polymerization of the γ,δ-epoxyalkene reactant in a manner analogous to the formation of polyether oligomers and polymers from ethylene oxide and propylene oxide.

Advantages provided by the continuous process disclosed herein include milder reaction conditions, simplified product separation and the ability to remove and replenish the catalyst system. The use of a mixture of the 2,5-dihydrofuran product and an oligomer of the γ,δ-epoxyalkene reactant as the inert process solvent allows the reaction to be run at temperatures substantially lower than those used in vapor phase processes wherein the catalyst is used as a molten salt or supported film using a gaseous carrier. As a result, the potential for catalyst deactivation or decomposition and by-product formation is decreased.

The γ,δ-epoxyalkene reactants may contain from 4 to about 8 carbon atoms. Examples of the epoxyalkene and epoxycycloalkene reactants include compounds having the structural formula:

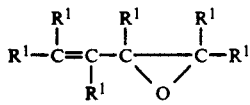
(I)

wherein each $R^1$ is independently selected from hydrogen and methyl or 2 $R^1$ substituents collectively may represent an alkylene radical which with the carbon atoms to which they are attached forms a cycloalkene group having about 5 to 8 carbon atoms. The preferred epoxyalkene reactants comprise compounds of formula (I) wherein a maximum of four of the $R^1$ substituents individually may represent methyl. Exemplary compounds contemplated for use in the practice of the present invention include 3,4-epoxy-3-methyl-1-butene, 3,4-epoxy-2-methyl-1-butene, 2,3-dimethyl-3,4-epoxy-1-butene, 3,4-epoxy-1-butene, 2,5-dimethyl-2,4-hexadiene monoepoxide, 3,4-epoxycyclooctene and the like. The epoxyalkene reactant of primary interest is 3,4-epoxy-1-butene.

The 2,5-dihydrofuran compounds obtained in accordance with our novel process have the structural formula:

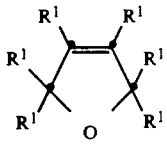
(II)

wherein the $R^1$ substituents are defined above. Of the compounds which may be obtained in accordance with our invention, the most important is 2,5-dihydrofuran.

The quaternary onium iodide compounds which may be used as the catalyst in our novel process are known compounds and,/or may be prepared according to published procedures. See, for example, U.S. Pat. No. 3,992,432 and the references cited therein. Exemplary quaternary organic onium iodide compounds include tetra-substituted quaternary onium iodides, wherein said substituents are selected from alkyl or substituted alkyl groups, cycloalkyl or substituted cycloalkyl groups, carbocyclic aryl or substituted carbocyclic aryl groups, heteroaryl or substituted heteroaryl groups, wherein each of said substituents may be bonded to one another to form a cyclic, heterocyclic, polycyclic or poly-heterocyclic structure. The onium iodide compounds normally should contain at least 6, and preferably at least 12, carbon atoms.

Examples of the onium iodide catalysts are compounds conforming to the formulas $(R^2)_4Y^+ \ I^-$,  (III)

$I^- \ (R^2)_3Y^+ - R^3 - Y^{+x}(R^2)_{2+x} \ I_x^-$,  (IV)

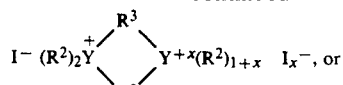

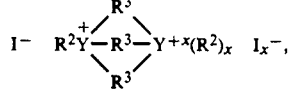

wherein
each $R^2$ independently is selected from alkyl or substituted alkyl moieties having up to about 20 carbon atoms, cycloalkyl or substituted cycloalkyl having about 5 to 20 carbon atoms, or aryl or substituted aryl having about 6 to 20 carbon atoms; or when Y is P, each $R^2$ also may be selected from alkoxy of up to about 20 carbon atoms, cycloalkoxy of about 5 to 20 carbon atoms, aryloxy of 6 to 10 carbon atoms or halogen;

two or three $R^2$ substituents collectively may represent joined hydrocarbylene groups, e.g. alkylene having 4 to 6 main chain carbon atoms or unsaturated groups such as —CH=CHCH=CHCH= and lower alkyl substituted alkylene and unsaturated groups, which form a mono- or polycyclic ring with the Y atom to which they are bonded;

each $R^3$ is independently selected from hydrocarbylene moieties or substituted hydrocarbylene moieties;

x is 0 or 1, and

Y is N, P or As; provided that the quaternary onium iodide compound contains at least 6 carbon atoms.

The substituted groups and moieties referred to above may bear one or more substituents such as groups having the formulas

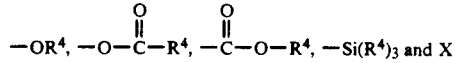

wherein each $R^4$ is independently selected from hydrogen or alkyl of up to about 20 carbon atoms and X is halogen. As used herein, the terms "hydrocarbylene moieties" refers to alkylene moieties having up to about 6 carbon atoms and arylene or polyarylene moieties having 6 to 20 carbon atoms.

The preferred onium iodide catalysts are the quaternary ammonium and, especially, the quaternary phosphonium iodide compounds. Exemplary ammonium compounds include tetrapentylammonium iodide, tetrahexylammonium iodide, tetraoctylammonium iodide, tetradecylammonium iodide, tetradodecylammonium iodide, tetrapropylammonium iodide, tetrabutylammonium iodide, N-octylquinuclidinium iodide, N,N'-dimethyl-N,N'-dihexadecylpiperazinium diiodide, dimethyl(hexadecyl)(3-pyrrolidinylpropyl)ammonium iodide, N,N,N,N',N',N'-hexa(dodecyl)octane-1,8-diammonium diiodide, N,N,N,N',N',N'-hexa(dodecyl)butane-1,4-diammonium diiodide, N-octylpyridinium iodide, and the like.

Exemplary phosphonium compounds include tetraoctylphosphonium iodide, tetrabutylphosphonium iodide, triphenyl(hexyl)phosphonium iodide, triphenyl(octyl)phosphonium iodide, tribenzyl(octyl)phosphonium iodide, tribenzyl(dodecyl)phosphonium iodide, triphenyl(decyl)phosphonium iodide, triphenyl(dodecyl)phosphonium iodide, tetrakis(2-methylpropyl)phosphonium iodide, tris(2-methylpropyl)(butyl)phosphonium iodide, tetradodecylphosphonium iodide, tetrahexadecylphosphonium iodide, trioctyl(octadecyl)phosphonium iodide, triphenyl(3,3-dimethylbutyl)phosphonium iodide, triphenyl(3-methylbutyl)phosphonium iodide, tris(2-methylbutyl)(3-methylbutyl)phosphonium iodide, triphenyl[2-trimethylsilylethyl)phosphonium iodide, tris(p-chlorophenyl)(dodecyl)phosphonium iodide, hexyl-tris(2,4,6-trimethylphenyl)phosphonium iodide, tetradecyltris(2,4,6-trimethylphenyl)phosphonium iodide, dodecyltris(2,4,6-trimethylphenyl)phosphonium iodide, and the like.

Tetra-substituted ammonium and phosphonium iodide compounds containing a total of about 16 to 64 carbon atoms are especially preferred. Such compounds have the formulas

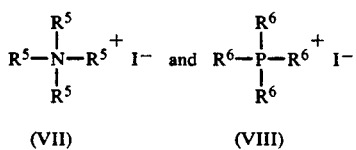

(VII)     (VIII)

wherein
each $R^5$ substituent independently is selected from alkyl of up to about 20 carbon atoms and each $R^6$ substituent is independently selected from $R^5$, benzyl, phenyl or phenyl substituted with up to 3 substituents selected from lower alkyl (alkyl of up to about 4 carbon atoms) lower alkoxy or halogen; or two $R^5$ substituents collectively may represent alkylene of 4 to 6 carbon atoms including alkylene of 4 to 6 carbon atoms substituted with lower alkyl; provided, as specified above, that the quaternary iodide compounds contain about 16 to 64 carbon atoms.

The onium iodide compounds described hereinabove are employed in combination with a Lewis acid to catalyze the isomerization process of our invention. Examples of inorganic Lewis acid co-catalysts include the alkali metal halides, zinc halides, tin (II) halides, tin (IV) halides, titanium (IV) halides, titanium (IV) tetra-loweralkoxides, zirconium (IV) halides, manganese (II) halides, iron (III) halides, or iron (III) acetylacetonate. Preferred inorganic Lewis acid co-catalysts comprise the alkali metal iodides, zinc iodide, zinc chloride, tin (II) iodide, tin (IV) iodide, titanium (IV) iodide, titanium (IV) tetramethoxide, titanium (IV) tetraethoxide, titanium (IV) tetraisopropoxide, zirconium (IV) iodide, manganese (II) iodide, manganese (II) chloride, iron (III) iodide, iron (III) acetylacetonate or a combination thereof. The inorganic Lewis acid co-catalysts which are particularly preferred are polarizable iodides, such as, for example, titanium (IV) iodide, zirconium (IV) iodide, and, especially, zinc iodide and tin (II) iodide.

The Lewis acid co-catalyst preferably is selected from organotin (IV) and organoantimony (V) compounds such as hydrocarbyltin trihalides, dihydrocarbyltin dihalides, trihydrocarbyltin halides, tetrahydrocarbyltin compounds and tetrahydrocarbylantimony halides. Examples of such organometallic compounds include compounds having the formula

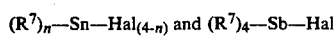

wherein
each $R^7$ independently is selected from alkyl or substituted alkyl moieties having up to about 20 carbon atoms, cycloalkyl or substituted cycloalkyl having about 5 to 20 carbon atoms, carbocyclic aryl or substituted carbocyclic aryl having about 6 to 20 carbon atoms, or heteroaryl or substituted heteroaryl moieties having about 4 up to 20 carbon atoms;

Hal is a halogen atom such as chloro, bromo or, preferably, iodo; and n is 1, 2, 3 or 4. Examples of organometallic compounds include dibutyltin diiodide, tributyltin iodide, trioctyltin iodide, triphenyltin iodide, tributyltin bromide, trimethyltin iodide, butyltin triiodide, tetrabutyltin, tetraoctyltin, tetraphenyltin, tricyclohexyltin iodide, tris-(2-methyl-2-phenylpropyl)tin iodide, tribenzyltin iodide, dimethyltin diiodide, diphenyltin diiodide, triphenyltin chloride, triphenyltin bromide and tetraphenylantimony iodide.

The preferred organometallic compounds comprise. trihydrocarbyltin (IV) iodides having a total carbon content of about 3 to 30 carbon atoms wherein, with reference to the above general formula, each $R^7$ substituent independently is selected f rom alkyl of up to about 12 carbon atoms, cycloalkyl of 5 to 7 carbon atoms, benzyl, 2-methyl-2-phenylpropyl, phenyl or phenyl substituted with up to 3 substituents selected from lower alkyl, lower alkoxy or halogen;

Hal is iodo; and
n is 3.

The catalyst system which is particularly preferred in the isomerization process provided by the present invention comprises a combination of (i) quaternary phosphonium iodide compounds containing a total of about 16 to 64 carbon atoms and (ii) organotin iodide compounds having the general formulas:

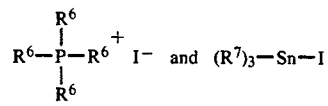

wherein each $R^6$ substituent is independently selected from alkyl of up to about 20 carbon atoms, benzyl, phenyl or phenyl substituted with up to 3 substituents selected from lower alkyl, lower alkoxy or halogen and each $R^7$ substituent is independently selected f rom alkyl of up to about 12 carbon atoms, benzyl, 2-methyl-2-phenylpropyl, phenyl or phenyl substituted with up to 3 substituents selected from lower alkyl, lower alkoxy or halogen.

The ratio of the onium iodide and Lewis acid components of the catalyst system can vary substantially depending, for example, upon the particular compounds used. Generally, the quaternary onium iodide:Lewis acid mole ratio is within the range of about 100:1 to 0.02:1. For catalyst systems comprising a quaternary onium iodide and an inorganic Lewis acid, the onium iodide:Lewis acid mole ratio preferably is in the range of about 100:1 to 2:1 and most preferably in the range of about 20:1 to 5:1. For catalyst systems comprising a quaternary onium iodide and an organometallic Lewis acid, the onium iodide:Lewis acid mole ratio preferably is in the range of about 20:1 to 0.05:1 and most preferably in the range of about 10:1 to 0.1:1. For the preferred catalyst system comprising a phosphonium iodide and an organotin iodide, a phosphonium iodide:organotin iodide mole ratio of about 5:1 to 0.2:1 is especially preferred.

The following are specific examples of the catalyst systems described above wherein the mole ratio of the components is normalized to 1.0 mole of the onium iodide:

(1) Tetradodecylammonium iodide (1.0 mole) and zinc iodide (0.05 mole)
(2) Triphenyl(hexyl)phosphonium iodide (1.00 mole) and zinc iodide (0.007 mole)
(3) Triphenyl(hexyl)phosphonium iodide (1.00 mole), tris-(2,4,6-trimethylphenyl)(hexyl)phosphonium iodide (0.77 mole) and zinc iodide (0.015 mole)
(4) Tetradodecylammonium iodide (1.00 mole) and tributyltin iodide (0.045 mole)
(5) Tetradodecylammonium iodide (1.00 mole) and dibutyltin diiodide (0.05 mole)
(6) Tetradodecylammonium iodide (1.00 mole) and triphenyltin iodide (0.05 mole)
(7) Triphenyl(hexyl)phosphonium iodide (1.00 mole) and tributyltin iodide (0.007 mole)
(8) Triphenyl(hexyl)phosphonium iodide (1.00 mole) and dibutyltin diiodide (0.02 mole)
(9) Tetradodecylammonium iodide (1.00 mole) and trioctyltin iodide (0.05 mole)
(10) Triphenyl(hexyl)phosphonium iodide (1.00 mole) and trioctyltin iodide (0.02 mole)
(11) Tetrabutylarsonium iodide (1.00 mole) and trioctyltin iodide (0.05 mole)
(12) Tetraoctylarsonium iodide (1.00 mole) and trioctyltin iodide (0.05 mole)
(13) Triphenyl(hexyl)phosphonium iodide (1.00 mole) and triphenyltin iodide (0.02 mole)
(14) Triphenyl(hexyl)phosphonium iodide (1.00 mole) and triphenyltin iodide (0.05 mole)
(15) Triphenyl(hexyl)phosphonium iodide (1.00 mole) and triphenyltin iodide (0.20 mole)
(16) Triphenyl(hexyl)phosphonium iodide (1.00 mole) and triphenyltin iodide (1.00 mole)
(17) Triphenyl(hexyl)phosphonium iodide (1.00 mole) and triphenyltin iodide (5.00 mole)
(18) Triphenyl(hexyl)phosphonium iodide (1.00 mole) and triphenyltin iodide (20.00 mole)
(19) Triphenyl(hexyl)phosphonium iodide (1.00 mole) and triphenyltin iodide (100.0 mole)
(20) Triphenyl(hexyl)phosphonium iodide (1.00 mole) and tricyclohexyltin iodide (5.00 mole)
(21) Triphenyl(hexyl)phosphonium iodide (1.00 mole) and tribenzyltin iodide (5.00 mole)
(22) Tetradodecylphosphonium iodide (1.00 mole) and triphenyltin iodide (1.00 mole)
(23) Trioctyl(octadecyl)phosphonium iodide (1.00 mole) and triphenyltin iodide (1.00 mole)
(24) Trioctyl(octadecyl)phosphonium iodide (1.00 mole) and trioctyltin iodide (1.00 mole)

As is specified hereinabove, the catalyst system constitutes about 10 to 95 weight percent of the liquid phase contained within the reaction zone. Preferably, the catalyst system constitutes about 50 to 90 weight percent of the liquid phase reaction mixture.

After start-up and during continuous operation of the process of the present invention, the solvent system comprises a mixture of the 2,5-dihydrofuran product and the oligomer of the $\gamma,\delta$-epoxyalkene reactant wherein the dihydrofuran:oligomer weight ratio is in the range of about 20:1 to 1:50. However, dihydrofuran:oligomer weight ratios in the range of about 2:1 to 1:20 are more typical. As is apparent to those skilled in the art, neither the oligomer nor the 2,5-dihydrofuran need be present at the start-up of the process.

Since the non-volatile oligomer accumulates in the reaction zone during the operation of the process, it is necessary to continuously or intermittently remove (purge) a portion of the oligomer-containing, liquid phase in the reaction zone from the production system to maintain acceptable production rates. The predetermined concentration of the catalyst system in the reaction zone may be maintained by feeding the catalyst components as a solution in the dihydrofuran being produced.

The continuous, liquid phase process of the present invention comprises either a vapor take-off or liquid take-off mode of operation. The vapor take-off embodiment of the process comprises the steps of:

(1) continuously feeding a $\gamma,\delta$-epoxyalkene to a reaction zone in which the catalyst components are dissolved in a process solvent comprising a mixture of the 2,5-dihydrofuran product and an oligomer of the $\gamma,\delta$-epoxyalkene reactant; and
(2) continuously removing from the reaction zone a vapor rich in the 2,5-dihydrofuran product;

wherein the catalyst components comprise (i) an onium iodide and (ii) a Lewis acid selected from inorganic. Lewis acids, an organotin (IV) compound, an organostibonium compound or a mixture thereof; the concentration of the catalyst system in the reaction zone liquid is maintained at about 10 to 95 weight percent, based on the total weight of the reaction zone liquid; and the liquid phase of the reaction zone is maintained at a temperature of about 65° to 160° C. In this mode of operation, the liquid phase reaction mixture is maintained at an elevated temperature to provide a vapor effluent comprising 2,5-dihydrofuran product while the non-volatile catalyst components and oligomer process solvent remain in the reaction mixture. The particular temperature at which the liquid reaction mixture is maintained to generate the vapor effluent depends on the particular epoxyalkene reactant fed and the pressure maintained within the reaction zone. Typically, the temperature is within about 65° to 160° C. with a temperature of about 80 to 1200C being preferred for the isomerization of 3,4-epoxy-1-butene to 2,5-dihydrofuran. The reaction zone may be maintained at pressures moderately below or above atmospheric pressure, e.g., from about 0.3 to 4.5 bars absolute, although excellent production rates are achieved at ambient pressure.

When only the $\gamma,\delta$-epoxyalkene reactant is fed to the reaction zone from which a vapor effluent is removed, the 2,5-dihydrofuran product obtained typically contains approximately 5 or more weight percent of unconverted reactant. This product mixture may be hydrogenated in the presence of a nickel catalyst as described in U.S. Pat. No. 4,962,210 to obtain a mixture of tetrahydrofuran and 1-butanol which may be separated by distillation. To maximize the conversion of the $\gamma,\delta$-epoxyalkene reactant to the 2,5-dihydrofuran product, at least 50 weight percent, preferably about 70 to 90 weight percent, of the reactor product effluent may be condensed and recycled to the reaction zone. The recycle of the product effluent results in conversions of $\gamma,\delta$-epoxyalkene reactant to 2,5-dihydrofuran product of 98 mole percent or greater and a 2,5-dihydrofuran product containing less than about 2 weight percent of $\gamma,\delta$-epoxyalkene reactant.

The liquid take-off mode of operation comprises the steps of:

(1) continuously feeding a homogeneous mixture comprising a $\gamma,\delta$-epoxyalkene reactant and the liquid phase of step (3)(b) to a reaction zone;

(2) continuously removing from the reaction zone a homogeneous liquid comprising a 2,5-dihydrofuran product, an oligomer of the γ,δ-epoxyalkene reactant and the catalyst components, and (3) continuously feeding the homogeneous liquid of step (2) to a distillation zone to obtain:

(a) a vapor phase rich in the 2,5-dihydrofuran product; and (b) a liquid phase comprising an oligomer of the γ,δ-epoxyalkene reactant and the catalyst components; wherein the catalyst components comprise (i) an onium iodide and (ii) a Lewis acid selected from inorganic Lewis acids, an organotin (IV) compound, an organostibonium compound or a mixture thereof; the concentration of the catalyst system in the reaction zone liquid is maintained at about 10 to 95 weight percent, based on the total weight of the reaction zone liquid; and the liquid phase of the reaction zone is maintained at a temperature of about 65° to 160° C.

The liquid phase of step (3)(b) typically contains a minor amount of the 2,5-dihydrofuran product. The reaction zone preferably comprises a plurality of reactors arranged in series wherein at least 90 weight percent, preferably at least 98 weight percent of the γ,δ-epoxyalkene reactant is converted to products. The temperature and pressure within the reaction zone are maintained within the ranges described hereinabove relative to the vapor take-off mode of operation.

Our novel process is further illustrated by the following examples. The apparatus used in Examples 1 and 2 consisted of a 1-L, glass kettle (reactor), a glycol-cooled condenser, a receiver, a recycle tank and a product tank. The reactor was fitted with a heating mantle, mechanical stirrer, liquid feed tube, thermometer and distillation head from which vapor was fed to the condenser. Gas chromatographic analyses were performed on a Hewlett Packard 5890A Gas Chromatograph, using a DB-1 fused silica capillary column (0.50 millimeter internal diameter by 15 meters). The oven was operated at 40° C. for 3 minutes, then heated to 185° C. at a rate of 20° C. per minute. Unless stated otherwise, analytical results are reported as area percentages in the examples.

EXAMPLE 1

Triphenyltin iodide (400 g) and triphenyl(n-hexyl)phosphonium iodide (200 g) were placed in the reactor and heated until the solids had melted (about 130° C.). Pumping of 2,5-dihydrofuran product from the recycle tank into the reactor was then begun at a rate of 580 mL per hour and the temperature was allowed to decrease to 90° C. 3,4-Epoxy-1-butene then was fed into the reactor at 145 mL per hour while maintaining the temperature at about 90° C. and the 2,5-dihydrofuran product feed (recycle) at 580 mL per hour. A vapor product stream was removed continuously from the reactor, condensed and the condensed liquid product flowed first to the receiver and then to the product recycle tank. The average rate of the product stream was 2.5 g 3,4-epoxy-1-butene and 661.3 g 2,5-dihydrofuran per hour. The portion of the product stream not recycled from the recycle tank to the reactor was allowed to overflow into a product tank. During the operation of the process, samples of the product stream were removed periodically just below the condenser and analyzed by gas chromatography. During a run of 195 hours, the spacetime yield of the net 2,5-dihydrofuran produced was approximately 400 g/L-hour and the average composition of the product distilled out of the reactor was 0.6% 3,4-epoxy-1-butene, 98.3% 2,5-dihydrofuran, 0.2% 2,3-dihydrofuran and 0.9% crotonaldehyde.

EXAMPLE 2

Tetra-n-dodecylammonium iodide (200 g), zinc iodide (10 g) and 2,5-dihydrofuran (100 mL) were placed in the reactor and the mixture was heated to 90° C. 3,4-Epoxy-1-butene was fed to the stirred homogeneous solution at a rate of 80 mL per hour, along with recycled 2,5-dihydrofuran product at a rate of 160 mL per hour. Samples were taken periodically from the distillate from the reactor for analysis by gas chromatography. The composition of the distillate was about 13% 3,4-epoxy-1-butene, 86% 2,5-dihydrofuran, and 1% crotonaldehyde.

EXAMPLE 3

Triphenyltin iodide (10.1 g) and triphenyl(n-hexyl)phosphonium iodide (10.3 g) were placed in a 100-mL, four-neck, round-bottom flask equipped with a thermometer, magnetic stirrer, distillation head, heating mantle and feed tube. After melting the catalyst components at about 125° C., 3,4-epoxy-3-methyl-1-butene (16.5 g) was pumped into the flask over 30 minutes while the reaction mixture was heated at 110 to 132° C. The distillate collected from the flask weighed 10.7 g and comprised 71.9% 3-methyl-2,5-dihydrofuran and 24.0% 2-methyl-2-butenal.

EXAMPLE 4

Triphenyltin iodide (24.9 g), tetradodecylphosphonium iodide (52.4 g) and 2,5-dihydrofuran (15.0 g) were placed in a 200-mL, four-neck, round-bottom flask equipped with a thermocouple, magnetic stirrer, distillation head, oil heating bath and reactant feed tube. The mixture was heated to 90° C. and the addition of 3,4-epoxy-1-butene was begun. The temperature was raised to and maintained at 105° C. Over a 38-hour period of continuous operation, 2350.1 g of 3,4-epoxy-1-butene were fed and 2235.6 g of distillate were recovered (95.1 weight percent recovery). The weight percent composition of the distillate was 6.65% 3,4-epoxy-1-butene, 92.2% 2,5-dihydrofuran and 1.13% crotonaldehyde.

EXAMPLE 5

Triphenyltin iodide (25.0 g), trioctyl(octyldecyl)phosphonium iodide (39.4 g) and 2,5-dihydrofuran (10.0 g) were placed in a 200-mL, four-neck, round-bottom flask equipped with a thermocouple, magnetic stirrer, distillation head, oil heating bath and reactant feed tube. The mixture was heated to 105° C. and the addition of 3,4-epoxy-1-butene was begun. Over a 40-hour period of continuous operation at 105° C., 2430.9 g of 3,4-epoxy-1-butene were fed and 2368.6 g of distillate were recovered (97.4 weight percent recovery). The weight percent composition of the distillate was 6.65% 3,4-epoxy-1-butene, 92.4% 2,5-dihydrofuran and 0.96% crotonaldehyde.

EXAMPLE 6

Trioctyltin iodide (30.7 g), trioctyl(octyldecyl)phosphonium iodide (39.6 g) and 2,5-dihydrofuran (9.9 g) were placed in a 200-mL, four-neck, round-bottom flask equipped with a thermocouple, magnetic stirrer, distillation head, oil heating bath and reactant feed tube. The mixture was heated to 105° C. and the addition of 3,4- epoxy-1-butene was begun. Over a 51-hour period of continuous operation at 105° C., 1400.5 g of 3,4-epoxy-1-butene were fed and 1336.9 g of distillate were recovered (95.5 weight percent recovery). The weight percent composition of the distillate was 8.32% 3,4-epoxy-1-butene, 90.9% 2,5-dihydrofuran and 0.79% crotonaldehyde.

EXAMPLE 7

The isomerization of 3,4-epoxy-1-butene to 2,5-dihydrofuran was conducted in a two-stage, continuous reaction system in which the product was distilled from the effluent from the second reactor and the catalyst was recycled to the first reactor. Each of the two reactors consisted of a one-liter, glass kettle fitted with a heating mantle, magnetic stirrer, thermometer, condenser, feed inlet and liquid takeoff tubes. Liquid reaction mixture was allowed to overflow the first reactor to the second reactor while maintaining a level of about 500 mL in the first reactor. The liquid takeoff from the second reactor was attached by way of a solenoid valve to a vacuum distillation apparatus. The solenoid valve was controlled by a level sensing device which could be adjusted to maintain a level of 250 to 500 mL in the second reactor by opening the solenoid valve to allow effluent to flow into the distillation column for removal of the product and any unreacted starting material.

The base pot of the distillation apparatus was fitted with a heating mantle and a side takeoff. The effluent from the pot was fed to the inlet of a pump for recirculation of the catalyst to the first reactor. All transfer lines were heated and insulated so that a temperature of about 90° C. was maintained. The reaction system was inventoried with a molten catalyst mixture composed of approximately equimolar quantities of triphenyltin iodide and trioctyl(octadecyl)phosphonium iodide. The reactors were heated to maintain a temperature 90°-95° C.

The catalyst recirculation pump was started so that the catalyst was fed to the inlet of the first reactor at a rate of 1000 to 1200 mL per hour. The amounts of catalyst components contained within the reactors during operation of the process were approximately 400 g trioctyl(octadecyl)phosphonium iodide and 255 g triphenyltin iodide. 3,4-Epoxy-1-butene was fed into the first reactor through a 300-mL bed of 3A molecular sieves at a rate of about 120 mL per hour. The reaction mixture was allowed to flow through the two reactors to the distillation column which was maintained at 280 to 305 torr and about 90° C. The distilled product was collected in a cooled receiver and the residual catalyst was allowed to flow from the base pot to the recirculation pump for return to the reactor. A small amount of oligomeric side-product was continually formed during the reaction. The amount of this material in the reaction mixture was allowed to increase to a level of 25 to 35 weight percent of the total. On startup, the level in the second reactor was kept at about 250 mL and then allowed to increase to about 500 mL as the amount of oligomer increased. The composition of the product 0.3% epoxybutene, 98.7% dihydrofuran and 1.0% crotonaldehyde.

The invention has been described in detail with particular reference to preferred embodiments thereof, but it will be understood that variations and modifications can be effected within the spirit and scope of the invention.

We claim:

1. Continuous process for the manufacture of a 2,5-dihydrofuran containing 4 to 8 carbon atoms by the steps comprising:
   (1) continuously feeding a $\gamma,\delta$-epoxyalkene to a reaction zone containing a solution of:
      (A) a catalytic amount of a catalyst system comprising (i) an onium iodide and (ii) a Lewis acid selected from inorganic Lewis acids, an organotin (IV) compound, an organostibonium compound or a mixture thereof; and
      (B) a process solvent system comprising the 2,5-dihydrofuran product and an oligomer of the $\gamma,\delta$-epoxyalkene reactant; and
   (2) continuously removing a vapor comprising the 2,5-dihydrofuran product from the reaction zone solution;

wherein the liquid phase of the reaction zone is maintained at a temperature of about 65° to 160° C. and the concentration of the catalyst system in the reaction zone liquid is maintained at about 10 to 95 weight percent, based on the total weight of the reaction zone liquid.

2. Process according to claim 1 for the manufacture of a 2,5-dihydrofuran containing 4 to 8 carbon atoms by the steps comprising:
   (1) continuously feeding a $\gamma,\delta$-epoxyalkene to a reaction zone in which the catalyst components are dissolved in a process solvent comprising a mixture of the 2,5-dihydrofuran product and an oligomer of the $\gamma,\delta$-epoxyalkene reactant; and
   (2) continuously removing from the reaction zone a vapor rich in the 2,5-dihydrofuran product;

wherein the catalyst components comprise (i) an onium iodide and (ii) a Lewis acid selected from inorganic Lewis acids, an organotin (IV) compound, an organostibonium compound or a mixture thereof; the concentration of the catalyst system in the reaction zone liquid is maintained at about 10 to 95 weight percent, based on the total weight of the reaction zone liquid; and the liquid phase of the reaction zone is maintained at a temperature of about 65° to 160° C.

3. Process according to claim 2 wherein the 2,5-dihydrofuran and the $\gamma,\delta$-epoxyalkene have the formulas

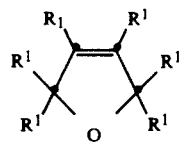

and

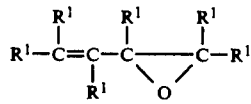

wherein each $R^1$ is independently selected from hydrogen and methyl.

4. Process according to claim 3 wherein the process is carried out at a temperature of about 80° to 120° C. and a pressure of about 0.3 to 4.5 bars absolute and not more than 4 of the $R^1$ substituents represent methyl.

5. Continuous process for the manufacture of a 2,5-dihydrofuran containing 4 to 8 carbon atoms and the formula

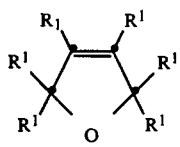

and

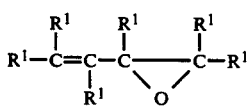

by the steps comprising:
(1) continuously feeding a γ,δ-epoxyalkene having the formula

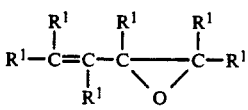

to a reaction zone containing a solution of:
(A) a catalytic amount of a catalyst system comprising (i) an onium iodide and (ii) an organotin (IV) compound; and
(B) a mixture of the 2,5-dihydrofuran product and an oligomer of the γ,δ-epoxyalkene reactant; and
(2) continuously removing a vapor comprising the 2,5-dihydrofuran from the reaction zone solution; wherein the liquid phase of the reaction zone is maintained at a temperature of about 65° to 160° C., the concentration of the catalyst system in the reaction zone liquid is maintained at about 50 to 90 weight percent, based on the total weight of the reaction zone liquid, and each $R^1$ substituent is independently selected from hydrogen and methyl.

6. Process according to claim 5 wherein the onium iodide is selected from compounds having the formula

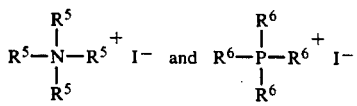

wherein
each $R^5$ substituent independently is selected from alkyl of up to about 20 carbon atoms and each $R^6$ substituent is independently selected from $R^5$, benzyl, phenyl or phenyl substituted with up to 3 substituents selected from lower alkyl, lower alkoxy or halogen; or
two $R^5$ substituents collectively may represent alkylene of 4 to 6 carbon atoms including alkylene of 4 to 6 carbon atoms substituted with lower alkyl, provided that the quaternary iodide compounds contain about 16 to 64 carbon atoms; and
the Lewis acid is selected from zinc iodide or tin (II) iodide.

7. Process according to claim 5 wherein the onium iodide is selected from compounds having the formula

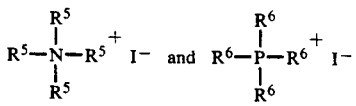

wherein
each $R^5$ substituent independently is selected from alkyl of up to about 20 carbon atoms and each $R^6$ substituent is independently selected from $R^5$, benzyl, phenyl or phenyl substituted with up to 3 substituents selected from lower alkyl, lower alkoxy or halogen; or
two $R^5$ substituents collectively may represent alkylene of 4 to 6 carbon atoms including alkylene of 4 to 6 carbon atoms substituted with lower alkyl, provided that the quaternary iodide compounds contain about 16 to 64 carbon atoms; and
the Lewis acid is selected from organotin (IV) and organoantimony (V) compounds having the formula

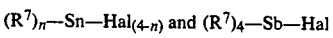

wherein
each $R^7$ independently is selected from alkyl or substituted alkyl moieties having up to about 20 carbon atoms, cycloalkyl or substituted cycloalkyl having about 5 to 20 carbon atoms, carbocyclic aryl or substituted carbocyclic aryl having about 6 to 20 carbon atoms, or heteroaryl or substituted heteroaryl moieties having about 4 up to 20 carbon atoms;
Hal is a halogen atom; and
n is 1, 2, 3 or 4.

8. Process according to claim 5 wherein the onium iodide is selected from quaternary phosphonium iodide compounds containing a total of about 16 to 60 carbon atoms having the formula:

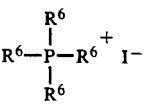

and the Lewis acid is selected from organotin iodide compounds having the formula:

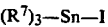

wherein each $R^6$ substituent is independently selected from alkyl of up to about 20 carbon atoms, benzyl, phenyl or phenyl substituted with up to 3 substituents selected from lower alkyl, lower alkoxy or halogen and each $R^7$ substituent is independently selected from alkyl of up to about 12 carbon atoms, benzyl, 2-methyl-2-phenylpropyl, phenyl or phenyl substituted with up to 3 substituents selected from lower alkyl, lower alkoxy or halogen; and
the mole ratio of the quaternary phosphonium iodide:organotin iodide is about 10:1 to 0.1:1.

9. Continuous process for the manufacture of 2,5-dihydrofuran by the steps comprising:
(1) continuously feeding 3,4-epoxy-1-butene to a reaction zone containing a solution of:
(A) a catalytic amount of a catalyst system comprising (i) a quaternary phosphonium iodide having a total of about 16 to 60 carbon atoms and the formula:

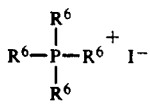

and (ii) an organotin (IV) compound having the formula:

$(R^7)_3-Sn-I$ wherein each $R^6$ substituent is independently selected from alkyl of up to about 20 carbon atoms, benzyl, phenyl or phenyl substituted with up to 3 substituents selected from lower alkyl, lower alkoxy or halogen; each $R^7$ substituent is independently selected from alkyl of up to about 12 carbon atoms, benzyl, 2-methyl-2-phenylpropyl, phenyl or phenyl substituted with up to 3 substituents selected from lower alkyl, lower alkoxy or halogen; and the mole ratio of (i):(ii) is about 10:1 to 0.1:1; and (B) a mixture of 2,5-dihydrofuran and an oligomer of 3,4-epoxy-1-butene; and (2) continuously removing a vapor comprising 2,5-dihydrofuran from the reaction zone;

wherein the liquid phase of the reaction zone is maintained at a temperature of about 80° to 120° C. and the concentration of the catalyst system in the reaction zone liquid is maintained at about 50 to 90 weight percent, based on the total weight of the reaction zone liquid.

10. Process according to claim 1 for the manufacture of a 2,5-dihydrofuran containing 4 to 8 carbon atoms by the steps comprising:

(1) continuously feeding a homogeneous mixture comprising a γ,δ-epoxyalkene reactant and the liquid phase of step (3)(b) to a reaction zone;

(2) continuously removing from the reaction zone a homogeneous liquid comprising a 2,5-dihydrofuran product, an oligomer of the γ,δ-epoxyalkene reactant and the catalyst components, and (3) continuously feeding the homogeneous liquid of step (2) to a distillation zone to obtain:
   (a) a vapor phase rich in the 2,5-dihydrofuran product; and
   (b) a liquid phase comprising an oligomer of the γ,δ-epoxyalkene reactant and the catalyst components;

wherein the catalyst components comprise (i) an onium iodide and (ii) a Lewis acid selected from inorganic Lewis acids, an organotin (IV) compound, an organostibonium compound or a mixture thereof; the concentration of the catalyst system in the reaction zone liquid is maintained at about 10 to 95 weight percent, based on the total weight of the reaction zone liquid; and the liquid phase of the reaction zone is maintained at a temperature of about 65° to 160° C.

11. Process according to claim 10 wherein the 2,5-dihydrofuran and the γ,δ-epoxyalkene have the formulas

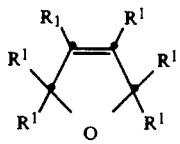

and

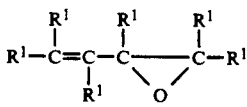

wherein each $R^1$ is independently selected from hydrogen and methyl.

12. Process according to claim 11 wherein the process is carried out at a temperature of about 80° to 120° C. and a pressure of about 0.3 to 4.5 bars absolute and not more than 4 of the $R^1$ substituents represent methyl.

13. Continuous process for the manufacture of a 2,5-dihydrofuran containing 4 to 8 carbon atoms and the formula

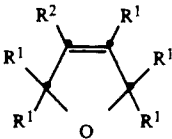

by the steps comprising:

(1) continuously feeding a homogeneous mixture comprising a γ,δ-epoxyalkene having the formula

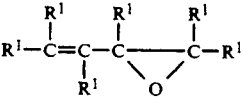

and the liquid phase of step (3)(b) to a reaction zone:

(2) continuously removing from the reaction zone a homogeneous liquid comprising a 2,5-dihydrofuran product having the formula

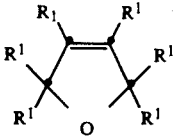

an oligomer of the γ,δ-epoxyalkene reactant and the catalyst components, and (3) continuously feeding the homogeneous liquid of step (2) to a distillation zone to obtain:
   (a) a vapor phase rich in the 2,5-dihydrofuran product; and
   (b) a liquid phase comprising the 2,5-dihydrofuran product, an oligomer of the γ,δ-epoxyalkene reactant and the catalyst components;

wherein the catalyst components comprise (i) an onium iodide and (ii) a Lewis acid selected from inorganic Lewis acids, an organotin (IV) compound, an organostibonium compound or a mixture thereof; the concentration of the catalyst system in the reaction zone liquid is maintained at about 10 to 95 weight percent, based on the total weight of the reaction zone liquid; and the liquid phase of the reaction zone is maintained at a temperature of about 65° to 160° C.

14. Process according to claim 13 wherein the onium iodide is selected from compounds having the formula

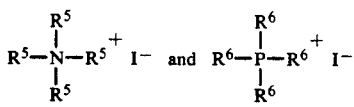

wherein
each $R^5$ substituent independently is selected from alkyl of up to about 20 carbon atoms and each $R^6$ substituent is independently selected from $R^5$, benzyl, phenyl or phenyl substituted with up to 3 substituents selected from lower alkyl, lower alkoxy or halogen; or two $R^5$ substituents collectively may represent alkylene of 4 to 6 carbon atoms including alkylene of 4 to 6 carbon atoms substituted with lower alkyl, provided that the quaternary iodide compounds contain about 16 to 64 carbon atoms; and the Lewis acid is selected from zinc iodide or tin (II) iodide.

15. Process according to claim 13 wherein the onium iodide is selected from compounds having the formula

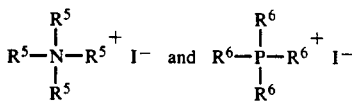

wherein
each $R^5$ substituent independently is selected from alkyl of up to about 20 carbon atoms and each $R^6$ substituent is independently selected from $R^5$, benzyl, phenyl or phenyl substituted with up to 3 substituents selected from lower alkyl, lower alkoxy or halogen; or two $R^5$ substituents collectively may represent alkylene of 4 to 6 carbon atoms including alkylene of 4 to 6 carbon atoms substituted with lower alkyl, provided that the quaternary iodide compounds contain about 16 to 64 carbon atoms; and the Lewis acid is selected from organotin (IV) and organoantimony (V) compounds having the formula

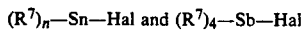

wherein
each $R^7$ independently is selected from alkyl or substituted alkyl moieties having up to about 20 carbon atoms, cycloalkyl or substituted cycloalkyl having about 5 to 20 carbon atoms, carbocyclic aryl or substituted carbocyclic aryl having about 6 to 20 carbon atoms, or heteroaryl or substituted heteroaryl moieties having about 4 up to 20 carbon atoms;

Hal is a halogen atom; and
n is 1, 2, 3 or 4.

16. Process according to claim 13 wherein the onium iodide is selected from quaternary phosphonium iodide compounds containing a total of about 16 to 60 carbon atoms having the formula:

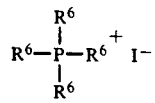

and the Lewis acid is selected from organotin iodide compounds having the formula:

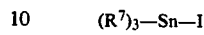

wherein each $R^6$ substituent is independently selected from alkyl of up to about 20 carbon atoms, benzyl, phenyl or phenyl substituted with up to 3 substituents selected from lower alkyl, lower alkoxy or halogen and each $R^7$ substituent is independently selected from alkyl of up to about 12 carbon atoms, benzyl, 2-methyl-2-phenylpropyl, phenyl or phenyl substituted with up to 3 substituents selected from lower alkyl, lower alkoxy or halogen; and the mole ratio of the quaternary phosphonium iodide:organotin iodide is about 10:1 to 0.1:1.

17. Process for the manufacture of 2,5-dihydrofuran by the steps comprising:
(1) continuously feeding a homogeneous mixture comprising 3,4-epoxy-l-butene and the liquid phase of step (3)(b) to a reaction zone;
(2) continuously removing from the reaction zone a homogeneous liquid comprising 2,5-dihydrofuran product, an oligomer of 3,4-epoxy-l-butene and catalyst components; and
(3) continuously feeding the homogeneous liquid of step (2) to a distillation zone to obtain:
  (a) a vapor phase rich in 2,5-dihydrofuran; and
  (b) a liquid phase comprising 2,5-dihydrofuran product, an oligomer of 3,4-epoxy-l-butene and catalyst components;
wherein the catalyst components comprise (i) a quaternary phosphonium iodide having a total of about 16 to 60 carbon atoms and the formula:

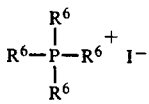

and (ii) an organotin (IV) compound having the formula:

wherein each $R^6$ substituent is independently selected from alkyl of up to about 20 carbon atoms, benzyl, phenyl or phenyl substituted with up to 3 substituents selected from lower alkyl, lower alkoxy or halogen; each $R^7$ substituent is independently selected from alkyl 6f up to about 12 carbon atoms, benzyl, 2-methyl-2-phenylpropyl, phenyl or phenyl substituted with up to 3 substituents selected from lower alkyl, lower alkoxy or halogen; and the mole ratio of (i):(ii) is about 10:1 to 0.1:1; the concentration of the catalyst system in the reaction zone liquid is maintained at about 50 to 95 weight percent, based on the total weight of the reaction zone liquid; and the liquid phase of the reaction zone is maintained at a temperature of about 80° to 120° C.

* * * * *

UNITED STATES PATENT AND TRADEMARK OFFICE
CERTIFICATE OF CORRECTION

PATENT NO. : 5,315,019
DATED : May 24, 1994
INVENTOR(S) : Gerald W. Phillips et al.

It is certified that error appears in the above-indentified patent and that said Letters Patent is hereby corrected as shown below:

Column 13, line 11 (Claim 5), please delete

"and

" .

Column 16, line 26 (Claim 13), after "and the formula",

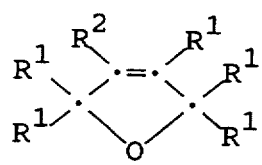

UNITED STATES PATENT AND TRADEMARK OFFICE
CERTIFICATE OF CORRECTION

PATENT NO. : 5,315,019
DATED : May 24, 1994
INVENTOR(S) : Gerald W. Phillips et al It is certified that error appears in the above-indentified patent and that said Letters Patent is hereby corrected as shown below:

should be

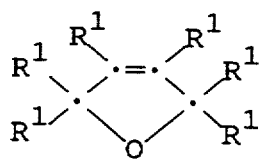

Signed and Sealed this

Thirtieth Day of August, 1994

Attest:

BRUCE LEHMAN

Attesting Officer

Commissioner of Patents and Trademarks